US009370308B2

(12) United States Patent
Addison et al.

(10) Patent No.: US 9,370,308 B2
(45) Date of Patent: Jun. 21, 2016

(54) ANGLE DISTRIBUTION TECHNIQUE FOR ANALYZING A PHYSIOLOGICAL SENSOR SIGNAL

(75) Inventors: Paul Addison, Midlothian (GB); James Ochs, Seattle, WA (US); James Watson, Fife (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 1009 days.

(21) Appl. No.: 13/461,002

(22) Filed: May 1, 2012

(65) Prior Publication Data

US 2013/0296659 A1    Nov. 7, 2013

(51) Int. Cl.
| | | |
|---|---|---|
| *A61B 5/1455* | (2006.01) | |
| *A61B 5/0205* | (2006.01) | |
| *A61B 5/029* | (2006.01) | |
| *A61B 5/00* | (2006.01) | |
| *A61B 5/021* | (2006.01) | |
| *A61B 5/024* | (2006.01) | |
| *A61B 5/08* | (2006.01) | |

(52) U.S. Cl.
CPC .............. *A61B 5/0205* (2013.01); *A61B 5/029* (2013.01); *A61B 5/02108* (2013.01); *A61B 5/02416* (2013.01); *A61B 5/0816* (2013.01); *A61B 5/14551* (2013.01); *A61B 5/7203* (2013.01); *A61B 5/7221* (2013.01)

(58) Field of Classification Search
CPC ..................................................... A61B 5/1455
See application file for complete search history.

(56) References Cited

U.S. PATENT DOCUMENTS

| | | | |
|---|---|---|---|
| 6,018,673 | A | 1/2000 | Chin et al. |
| 6,035,223 | A | 3/2000 | Baker, Jr. |
| 6,374,129 | B1 | 4/2002 | Chin et al. |
| 6,845,256 | B2 | 1/2005 | Chin et al. |
| 7,039,538 | B2 | 5/2006 | Baker, Jr. |
| 7,194,293 | B2 | 3/2007 | Baker, Jr. |
| 7,260,425 | B2 | 8/2007 | Chin et al. |
| 7,392,075 | B2 | 6/2008 | Baker, Jr. |
| 7,474,907 | B2 | 1/2009 | Baker, Jr. |
| 8,007,441 | B2 | 8/2011 | Baker, Jr. |
| 8,255,029 | B2 | 8/2012 | Addison et al. |
| 8,295,607 | B1 * | 10/2012 | Biswas et al. ................. 382/199 |
| 2002/0103423 | A1 | 8/2002 | Chin et al. |
| 2005/0070773 | A1 | 3/2005 | Chin et al. |
| 2005/0070775 | A1 | 3/2005 | Chin et al. |

(Continued)

FOREIGN PATENT DOCUMENTS

| | | |
|---|---|---|
| WO | 03/071938 A1 | 9/2003 |
| WO | 2004075746 A2 | 9/2004 |

OTHER PUBLICATIONS

International Search Report and Written Opinon for PCT Application No. PCT/US2013/039093 dated Sep. 12, 2013; 7 pgs.

*Primary Examiner* — Eric Winakur
*Assistant Examiner* — Marjan Fardanesh
(74) *Attorney, Agent, or Firm* — Fletcher Yoder PC

(57) ABSTRACT

The present disclosure relates generally to patient monitoring systems and, more particularly, to signal analysis for patient monitoring systems. In one embodiment, a method of analyzing a detector signal of a physiological patient sensor includes obtaining the detector signal from the physiological patient sensor, and determining a ratio of the signal between two or more channels. A distribution of the angles between the points of the ratio over time may be used to determine a true ratio or a ratio of ratios for use in the determination of a physiological parameter.

16 Claims, 9 Drawing Sheets

(56) References Cited

U.S. PATENT DOCUMENTS

| | | |
|---|---|---|
| 2005/0197579 A1 | 9/2005 | Baker, Jr. |
| 2006/0258921 A1 | 11/2006 | Addison et al. |
| 2006/0265022 A1 | 11/2006 | John et al. |
| 2007/0032733 A1 | 2/2007 | Burton |
| 2007/0299328 A1 | 12/2007 | Chin et al. |
| 2008/0077022 A1 | 3/2008 | Baker, Jr. |
| 2008/0255436 A1 | 10/2008 | Baker, Jr. |
| 2009/0275841 A1* | 11/2009 | Melendez et al. ............ 600/476 |
| 2009/0324033 A1 | 12/2009 | Addison et al. |
| 2009/0326867 A1 | 12/2009 | Watson et al. |
| 2010/0016680 A1 | 1/2010 | Addison et al. |
| 2013/0046156 A1 | 2/2013 | Addison et al. |

* cited by examiner

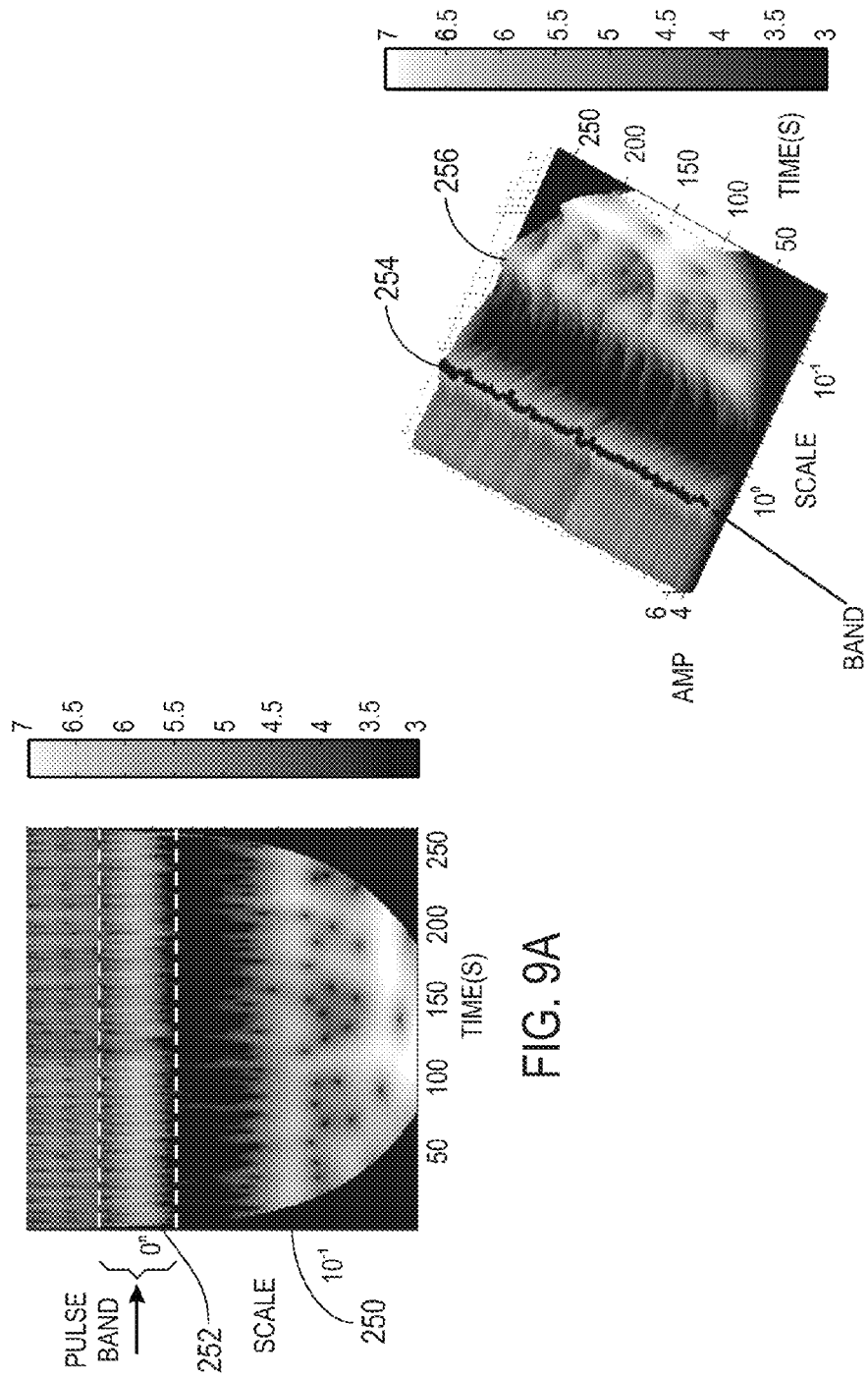

ANGLE DISTRIBUTION TECHNIQUE FOR ANALYZING A PHYSIOLOGICAL SENSOR SIGNAL

BACKGROUND

The present disclosure relates generally to patient monitoring systems and, more particularly, to signal processing techniques for patient monitoring systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors routinely desire to monitor certain physiological characteristics of their patients. Accordingly, a wide variety of systems and devices have been developed for monitoring many of these physiological characteristics. Generally, these patient monitoring systems provide doctors and other healthcare personnel with the information they need to provide the best possible healthcare for their patients. Consequently, such monitoring systems have become an indispensable part of modern medicine.

In general, these patient monitoring systems may include a patient sensor that has a detector (e.g., an optical or electrical detector) that is configured to perform a measurement on the tissue of a patient. However, the signal produced by the detector may suffer from various types of noise (e.g., electrical noise, interference, artifacts from patient activity, etc.). Such noise in a detector signal may introduce substantial complexity as well as possible inaccuracy into the determination of the physiological parameter of the patient. Further, the signal artifacts may be translated throughout the signal processing. As such, if a signal includes a substantial amount of noise it may be difficult to accurately calculate the physiological parameter of the patient using conventional methods.

BRIEF DESCRIPTION OF THE DRAWINGS

Advantages of the disclosed techniques may become apparent upon reading the following detailed description and upon reference to the drawings in which:

FIGS. 9A and 9B show illustrative views of a scalogram derived from a plethysmographic signal in accordance with an embodiment;

DETAILED DESCRIPTION OF SPECIFIC EMBODIMENTS

Figure 1:
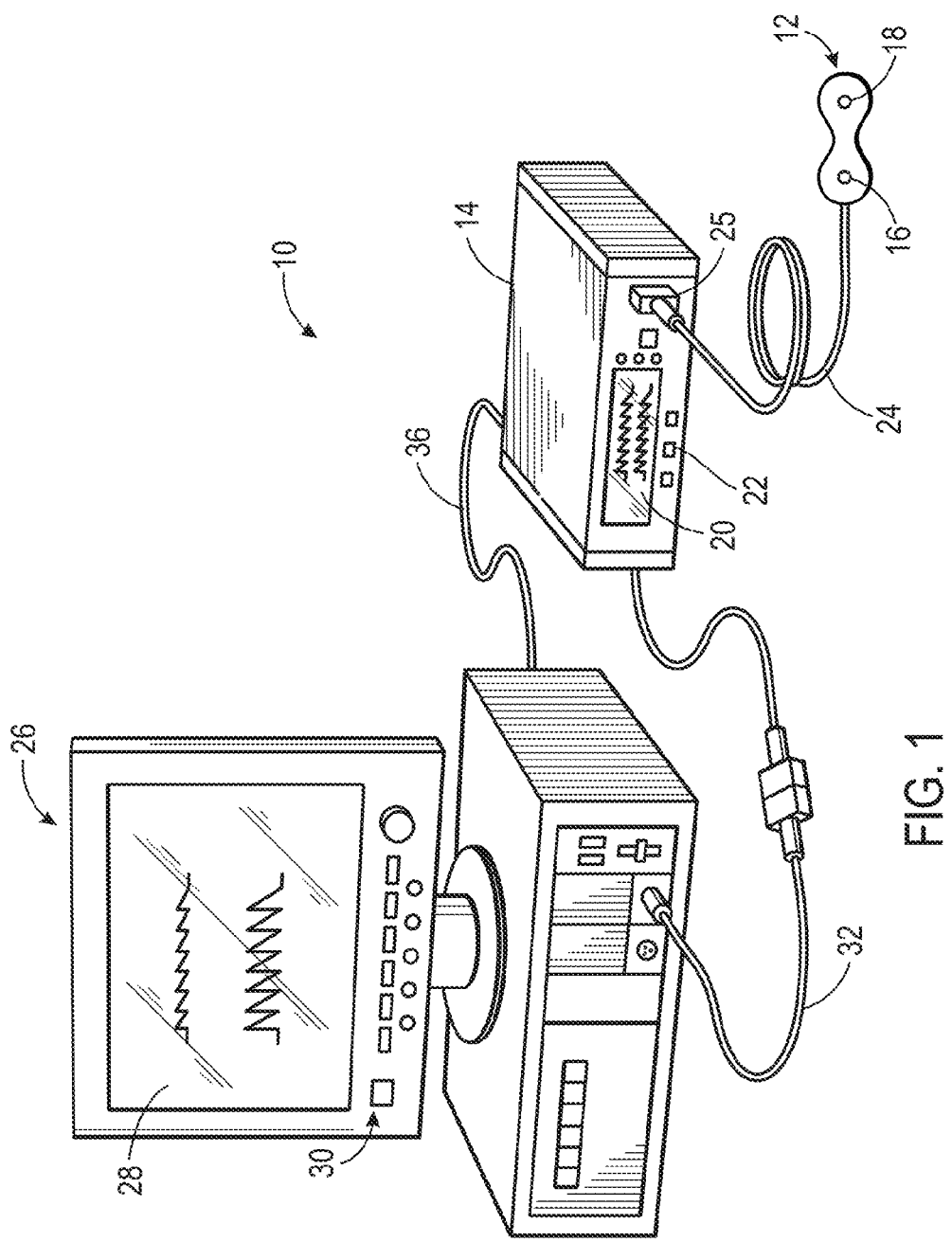
FIG. 1 illustrates a perspective view of a pulse oximeter, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Photoplethysmography is a noninvasive technique for monitoring physiological characteristics of a patient. In one example, a photoplethysmography device uses a sensor that transmits light through a patient's tissue and photoelectrically detects the absorption and/or scattering of the transmitted light in such tissue. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue or the blood oxygen saturation using various algorithms.

The photoplethysmography signal reflects pulsatile, dynamic changes in amount and type of blood constituents in tissue. However, the photoplethysmography signal may be sensitive to movement, and various types of motion may cause artifacts that may obscure the blood constituent signal. For example, motion artifacts may be caused by moving a sensor in relation to the tissue, by increasing or decreasing the physical distance between emitters and detectors in a sensor, by changing the direction of emitters or detectors with respect to tissue or each other, by changing the angles of incidence and interfaces probed by the light, by directing the optical path through different amounts or types of tissue, or by expanding, compressing or otherwise altering tissue near a sensor. These motions oftentimes have similar frequency content to the pulse, and may lead to similar or even larger optical modulations than the pulse. In addition, a photoplethysmography signal may be subject to electromagnetic interference.

Depending on the particular algorithms that are used to calculate the parameter of interest, certain types of signal artifacts may translate throughout the calculation, resulting in errors in the calculated parameter. In one example, a slope of a value calculated based on the plethysmographic signal over time is used as part of an algorithm to determine a physiological parameter. For example, in pulse oximetry, slope values along a plot of the red logarithmic signal versus the infrared logarithmic signal may be used for determining the ratio of ratios that in turn is part of the calculation of blood oxygen saturation. When the signal used as the basis for the slope calculation is noisy, i.e., containing sharp peaks and drop-offs as opposed to a smoother signal, the corresponding calculated slopes may reflect the noise rather than the signal. Noisy peaks approaching vertical may result in calculated slopes that are unbounded, i.e., infinite, and generally flat areas approach zero. Such signal artifacts and their resultant slope values may obscure the true, underlying slope that represents the parameter of interest, and may further result in other gradients tending to unity.

Provided herein are techniques that address the problems that may result when using slope values in a relatively noisy signal to determine a physiological parameter. Rather than calculating slope values, the present techniques involve calculating representative angles from each point along the plot to every other point along the curve. The calculated angles provide a distribution that allows modeling of the underlying peak in the distribution of values as well as a determination of the weighted mean of the distribution.

With this in mind, FIG. 1 depicts an embodiment of a patient monitoring system 10 that may be used in conjunction with a plethysmographic sensor 12. Although the depicted embodiments relate to relate to photoplethysmography or pulse oximetry, the system 10 may be configured to obtain a variety of medical measurements with a suitable medical sensor. The system 10 includes the sensor 12 that is communicatively coupled to a patient monitor 14. The sensor 12 includes one or more emitters 16 and one or more detectors 18. The emitters 16 and detectors 18 of the sensor 12 are coupled to the monitor 14 via a cable 24 through a plug 25 coupled to a sensor port. Additionally, the monitor 14 includes a monitor display 20 configured to display information regarding the physiological parameters, information about the system, and/or alarm indications. The monitor 14 may include various input components 22, such as knobs, switches, keys and keypads, buttons, etc., to provide for operation and configuration of the monitor. The monitor 14 also includes a processor that may be used to execute code such as code for implementing the techniques discussed herein.

The monitor 14 may be any suitable monitor, such as a pulse oximetry monitor available from Nellcor Puritan Bennett LLC. The monitor 14 may also be capable of determining a patient's respiration rate based on the plethysmographic waveform signal. Furthermore, to upgrade conventional operation provided by the monitor 14 to provide additional functions, the monitor 14 may be coupled to a multi-parameter patient monitor 26 via a cable 32 connected to a sensor input port or via a cable 36 connected to a digital communication port, or via an RF or optical wireless link. Alternatively, the techniques provided herein may be incorporated into one or more individual modules with plug-in connectivity to the multi-parameter patient monitor 26. Such modules may include connectors that allow the calculated physiological parameters to be sent to the host multi-parameter monitor. In addition, the monitor 14, or, alternatively, the multi-parameter patient monitor 26, may be configured to calculate physiological parameters and to provide a central display 28 for the visualization of information from the monitor 14 and from other medical monitoring devices or systems. The multi-parameter monitor 26 includes a processor that may be configured to execute code. The multi-parameter monitor 26 may also include various input components 30, such as knobs, switches, keys and keypads, buttons, etc., to provide for operation and configuration of the a multi-parameter monitor 26. In addition, the monitor 14 and/or the multi-parameter monitor 26 may be connected to a network to enable the sharing of information with servers or other workstations. In certain embodiments, the sensor 12 may be a wireless sensor 12. Accordingly, the wireless sensor 12 may establish a wireless communication with the patient monitor 14 and/or the multi-parameter patient monitor 26 using any suitable wireless standard. By way of example, the wireless module may be capable of communicating using one or more of the ZigBee standard, WirelessHART standard, Bluetooth standard, IEEE 802.11x standards, or MiWi standard. In embodiments in which the sensor 12 is configured for wireless communication, the strain relief features of the cable 24 may be housed in the sensor body 34.

As provided herein, the sensor 12 may be a sensor suitable for detection of one or more physiological parameters. The sensor 12 may include optical components (e.g., one or more emitters 16 and detectors 18). In one embodiment, the sensor 12 may be configured for photo-electric detection of blood and tissue constituents. For example, the sensor 12 may include pulse oximetry sensing functionality for determining the oxygen saturation of blood as well as other parameters (e.g., respiration rate, arrhythmia detection) from the plethysmographic waveform detected by the oximetry technique. An oximetry system may include a light sensor (e.g., sensor 12) that is placed at a site on a patient, typically a fingertip, toe, forehead or earlobe, or in the case of a neonate, across a foot. The sensor 12 may pass light using the emitter 16 through blood perfused tissue and photoelectrically sense the absorption of light in the tissue. For example, the monitor 14 may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (photoplethysmography) signal. The light intensity or the amount of light absorbed may then be used to calculate the amount of the blood constituent (e.g., oxyhemoglobin) being measured and other physiological parameters such as the pulse rate and when each individual pulse occurs. Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. At least two, e.g., red and infrared (IR), wavelengths may be used because it has been observed that highly oxygenated blood will absorb relatively less red light and more infrared light than blood with a lower oxygen saturation. However, it should be understood that any appropriate wavelengths, e.g., green, etc., may be used as appropriate. Further, photoplethysmography measurements may be determined based on one, two, or three or more wavelengths of light.

Figure 2:
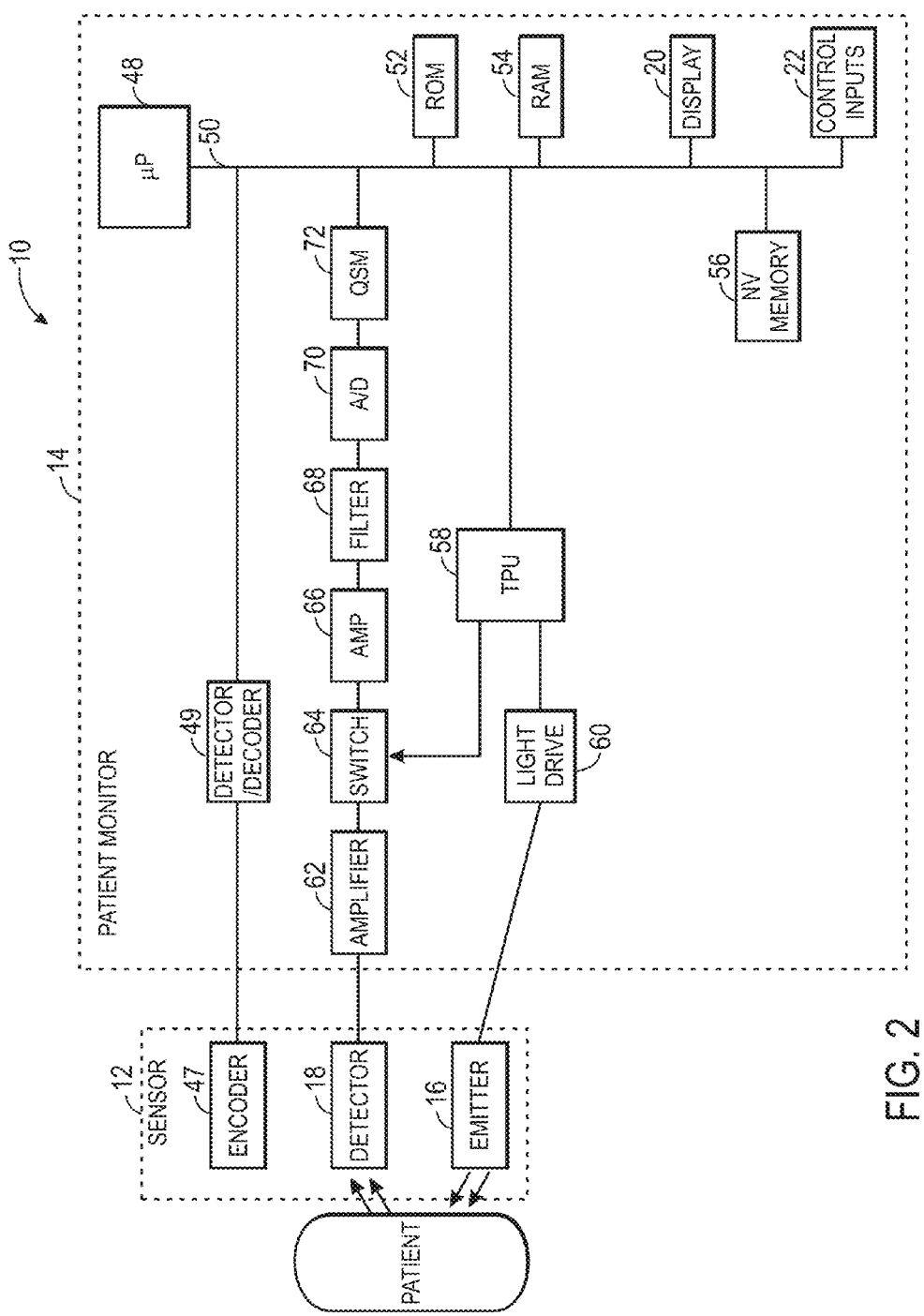
FIG. 2 illustrates a simplified block diagram of a pulse oximeter, in accordance with an embodiment of the present disclosure.

Turning to FIG. 2, a simplified block diagram of the medical system 10 is illustrated in accordance with an embodiment. As noted, the sensor 12 may include optical components in the forms of emitters 16 and detectors 18. The emitter 16 and the detector 18 may be arranged in a reflectance or transmission-type configuration with respect to one another. However, in embodiments in which the sensor 12 is configured for use on a patient's forehead (e.g. either alone or in conjunction with a hat or headband), the emitters 16 and detectors 18 may be in a reflectance configuration. Such sensors 12 may be used for pulse oximetry or regional saturation monitoring (e.g., INVOS® monitoring). An emitter 16 may also be a light emitting diode, superluminescent light emitting diode, a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements, absorptive filters, dielectric stack filters, or interferometers. These kinds of emitters and/or detectors would typically be coupled to the sensor 12 via fiber optics. Alternatively, a sensor assembly 12 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects in conjunction with the appropriate sensing elements.

In certain embodiments, the emitter 16 and detector 18 may be configured for pulse oximetry. It should be noted that the emitter 16 may be capable of emitting at least two wavelengths of light, e.g., red and infrared (IR) light, into the tissue of a patient, where the red wavelength may be between about 600 nanometers (nm) and about 700 nm, and the IR wavelength may be between about 800 nm and about 1000 nm. The emitter 16 may include a single emitting device, for example, with two LEDs, or the emitter 16 may include a plurality of emitting devices with, for example, multiple LED's at various locations. In some embodiments, the LEDs of the emitter 16 may emit three or more different wavelengths of light. Such wavelengths may include a red wavelength of between approximately 620-700 nm (e.g., 660 nm), a far red wavelength of between approximately 690-770 nm (e.g., 730 nm), and an infrared wavelength of between approximately 860-940nm (e.g., 900 nm). Other wavelengths may include, for example, wavelengths of between approximately 500-600 nm and/or 1000-1100 nm and/or 1200-1400 nm. Regardless of the number of emitting devices, light from the emitter 16 may be used to measure, as provided herein, a physiological parameter, such as a pulse rate, oxygen saturation, respiration rate, respiration effort, continuous non-invasive blood pressure, cardiac output, fluid responsiveness, perfusion, pulse rhythm type, hydration level, or any combination thereof. In certain embodiments, the sensor measurements may also be used for determining water fraction, hematocrit, or other physiologic parameters of the patient. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In another embodiment, two emitters 16 may be configured for use in a regional saturation technique. To that end, the emitters 16 may include two light emitting diodes (LEDs) that are capable of emitting at least two wavelengths of light, e.g., red or near infrared light. In one embodiment, the LEDs emit light in the range of 600 nanometers to approximately 1000 nm. In a particular embodiment, one LED is capable of emitting light at 730 nm and the other LED is capable of emitting light at 810 nm.

In any suitable configuration of the sensor 12, the detector 18 may be an array of detector elements that may be capable of detecting light at various intensities and wavelengths. In one embodiment, light enters the detector 18 after passing through the tissue of the patient. In another embodiment, light emitted from the emitter 16 may be reflected by elements in the patent's tissue to enter the detector 18. The detector 18 may convert the received light at a given intensity, which may be directly related to the absorbance and/or reflectance of light in the tissue of the patient, into an electrical signal. That is, when more light at a certain wavelength is absorbed, less light of that wavelength is typically received from the tissue by the detector 18, and when more light at a certain wavelength is reflected, more light of that wavelength is typically received from the tissue by the detector 18. The detector 18 may receive light that has not entered the tissue to be used as a reference signal. After converting the received light to an electrical signal, the detector 18 may send the signal to the monitor 14, where physiological characteristics may be calculated based at least in part on the absorption and/or reflection of light by the tissue of the patient.

In certain embodiments, the medical sensor 12 may also include an encoder 47 that may provide signals indicative of the wavelength of one or more light sources of the emitter 16, which may allow for selection of appropriate calibration coefficients for calculating a physical parameter such as blood oxygen saturation. The encoder 47 may, for instance, be a coded resistor, EEPROM or other coding devices (such as a capacitor, inductor, PROM, RFID, parallel resident currents, or a colorimetric indicator) that may provide a signal to a microprocessor 48 related to the characteristics of the medical sensor 12 to enable the microprocessor 48 to determine the appropriate calibration characteristics of the medical sensor 12. Further, the encoder 47 may include encryption coding that prevents a disposable part of the medical sensor 12 from being recognized by a microprocessor 48 unable to decode the encryption. For example, a detector/decoder 49 may translate information from the encoder 47 before it can be properly handled by the processor 48. In some embodiments, the encoder 47 and/or the detector/decoder 48 may not be present. In some embodiments, the encrypted information held by the encoder 47 may itself be transmitted via an encrypted data protocol to the detector/decoder 49, such that the communication between 47 and 49 is secured.

Signals from the detector 18 and/or the encoder 47 may be transmitted to the monitor 14. The monitor 14 may include one or more processors 48 coupled to an internal bus 50. Also connected to the bus may be a ROM memory 52, a RAM memory 54, non-volatile memory 56, a display 20, and control inputs 22. A time processing unit (TPU) 58 may provide timing control signals to light drive circuitry 60, which controls when the emitter 16 is activated, and if multiple light sources are used, the multiplexed timing for the different light sources. TPU 58 may also control the gating-in of signals from detector 18 through a switching circuit 64. These signals are sampled at the proper time, depending at least in part upon which of multiple light sources is activated, if multiple light sources are used. The received signal from the detector 18 may be passed through one or more amplifiers (e.g., amplifiers 62 and 66), a low pass filter 68, and an analog-to-digital converter 70 for amplifying, filtering, and digitizing the electrical signals from the sensor 12. The digital data may then be stored in a queued serial module (QSM) 72, for later downloading to RAM 54 as QSM 72 fills up. In an embodiment, there may be multiple parallel paths for separate amplifiers, filters, and A/D converters for multiple light wavelengths or spectra received.

Based at least in part upon the received signals corresponding to the light received by optical components of the pulse oximetry sensor 20, microprocessor 48 may calculate a oxygen saturation, respiration rate, and/or heart rate using various algorithms, such as those employed by the Nellcor™ N-600x™ pulse oximetry monitor, which may be used in conjunction with various Nellcor™ pulse oximetry sensors, such as OxiMax™ sensors. In addition, the microprocessor 48 may calculate and/or display trend or parameter variability using various methods, such as those provided herein. These algorithms may employ certain coefficients, which may be empirically determined, and may correspond to the wavelengths of light used. The algorithms and coefficients may be stored in a ROM 52 or other suitable computer-readable storage medium and accessed and operated according to microprocessor 48 instructions. In one embodiment, the correction coefficients may be provided as a lookup table.

Figure 3:
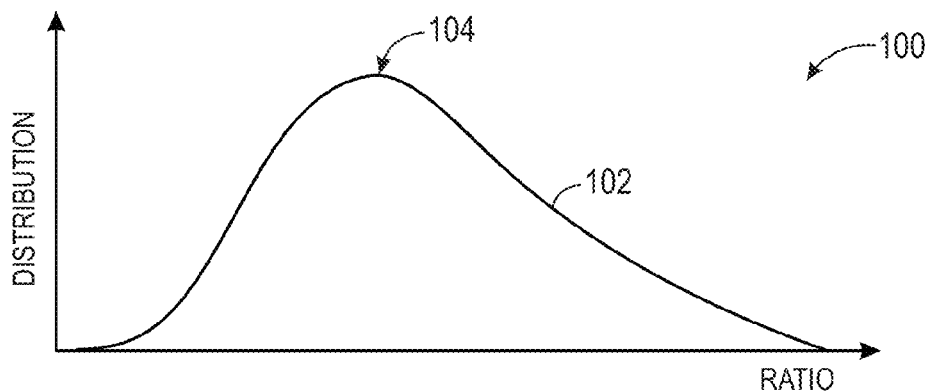
FIG. 3 illustrates an example of a slope distribution signal, in accordance with an embodiment of the present disclosure.

For example, in pulse oximetry applications of photoplethysmography, a ratio may be determined from components (e.g., channels of a multiplexed signal) of the received signal, such as the red and the infrared signals. This ratio may be used to determine the value of the patient's $SPO_2$ using a lookup table of coefficients. Typically, several ratios are computed over time and a representative ratio is then determined that is used to determine the $SPO_2$ value. A representative ratio may, for example, be derived by taking a mean value over a number of computed values, or a weighted mean, or a median value, or by use of another type of filtering, e.g., an IIR filter. In one embodiment, the ratio is determined over time based on a Lissajous plot of the red logarithmic signal versus the IR logarithmic signal. In another technique, a Lissajous plot is derived using wavelet transforms using the techniques discloses in U.S. Patent Application No. 20090326867 to Watson et al., which is incorporated by reference herein in its entirety for all purposes. A graph 100 of the distribution of the slopes (shown as distribution 102) determined from a Lissajous plot is illustrated in FIG. 3. The peak 104 of the distribution 102 may be used to determine the ratio.

Figure 4:
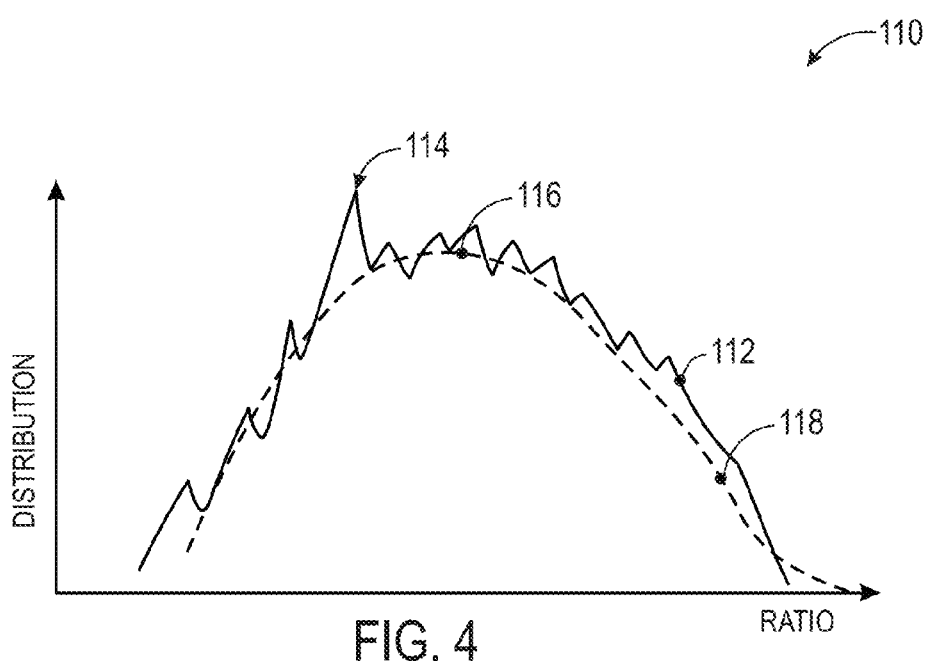
FIG. 4 is a graph illustrating a slope distribution of a noisy signal, in accordance with an embodiment of the present disclosure.

However, for noisy signals where there is a spread in values around the true value (i.e., without noise), the computed slope tends to infinity in value for slopes approaching vertical and to zero for slopes approaching horizontal. The actual slope at a point depends on which channel has noise, the amplitude of the noise, the polarity of that noise, etc. For such signals, the distribution peak may not accurately represent the location of true ratio. For example when a limited number of ratios are available, the distribution may be noisy. FIG. 4 is a graph 110 of a slope distribution 112 from a simulated noisy signal showing an artifact-biased peak value 114. The true peak 116 of the underlying distribution 118, which is the distribution calculated from a signal free from signal artifact, is also shown. As indicated in the calculated distribution 112 based on gradient values, the gradient distribution is highly nonlinear as gradients tending to the horizontal tend to zero; gradients tending to the vertical have gradients tending to infinity, and, in between, gradients an angle of $\pi/2$ radians tend to unity. Thus the gradient distribution may be skewed.

Figure 5:
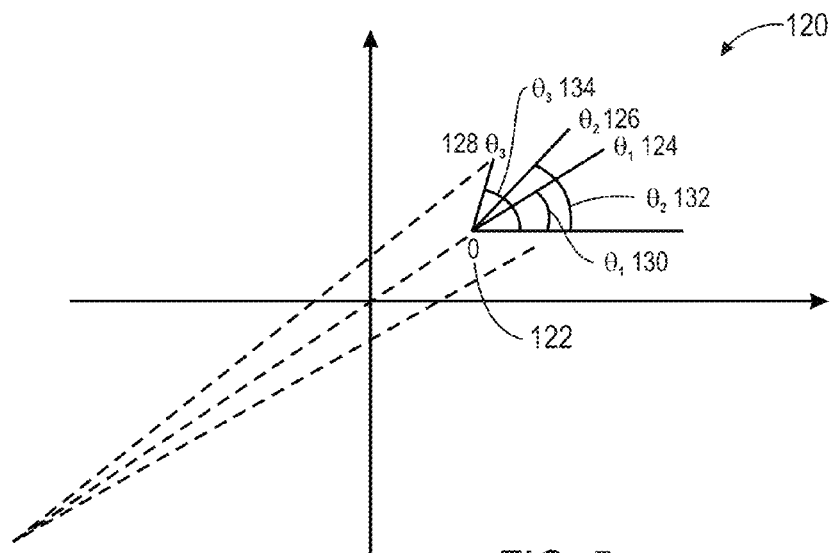
FIG. 5 is an example angle distribution plot.

As provided herein, a more accurate representation of the underlying distribution may be determined by calculating representative angles of from each point in a Lissajous plot to every other point. In certain embodiments, all angles are considered only to be in quadrant 1 and 4, i.e. from 0 to $+\pi/2$ and from 0 to $-\pi/2$ from each point-to-point pair. Computing the angles from point to point in the Lissajous is shown schematically in FIG. 5. In the schematic 120, the angles from an initial point on the Lissajous, denoted "0" and indicated by reference number 122, are computed to points 1, 2, and 3 (indicated as 124, 126, and 128, respectively) to give angles $\theta_1$ (indicated as 130), $\theta_2$ (indicated as 132), and $\theta_3$ (indicated as 134). In particular embodiments, this angle determination may take place between a selected subset of points or between all points. The designation of an individual point as "0" to determine the point-to-point angles may be performed in turn on all relevant points in a given ratio calculation and/or plot such as a Lissajous plot. Accordingly, a next point is considered and all the angles from it to all other points computed, and so on. The angles obtained are then used to form the distribution. When a peak detected in the distribution due to noise is not the underlying peak (see FIG. 4.), for example when a limited number of ratios are available the distribution may be noisy, the underlying distribution may be modeled to more accurately determine a peak using a simple mathematical model.

For example, a Gaussian distribution may be used assuming that the angle data is normally distributed due to the noise. In another embodiment, the underlying distribution may not be modeled. Instead, a weighted mean value of the center of the distribution may be used as a true peak of the distribution. In other embodiments, these techniques may be combined or compared as a measure of confidence in the determined value. For example, if the peak distribution and/or weighted mean value and the modeled peak determined by angle distribution strongly correlate, the measure may have higher confidence. In another embodiment, if the physiological parameters calculated by both methods strongly correlate, the measure may have higher confidence.

Further, the present techniques may also be used in combination with slope distribution methods. In one embodiment, a slope distribution technique for determining a physiological parameter may be used if a signal quality metric (e.g., a signal with a signal quality above a predetermined threshold) indicates a low degree of noise using any suitable signal quality metric or assessment, such as those provided in U.S. Pat. Nos. 7,474,907, 7,039,538, and 6,035,223, which are incorporated by reference in their entirety herein for all purposes. For example, signal quality may be assessed by pulse frequency that is correlated to a range of human heart rates, shape characteristics, rise time, pulse amplitude, or a combination thereof. The angle distribution technique may be used in instances of a noisy signal, e.g., if a signal quality metric is below a predetermined threshold. The present techniques may also calculate peaks and/or mean distribution values based on angle distribution and a slope distribution, and may arbitrate between these values based on the signal quality. In another embodiment, the system 10 may calculate two physiological parameter values based on angle distribution and a slope distribution, and may arbitrate between these values based on the signal quality. Further, a correlation or divergence between values (e.g., peaks or physiological parameters) calculated by these techniques may also be used as an indication of interference in the signal. In one embodiment, the higher the correlation, the higher the signal quality. A low correlation between these values may be an indicator of a noisy signal. The system 10 may provide an alarm or other indication relating to signal quality in the event of sufficient divergence between such values.

Figure 6:
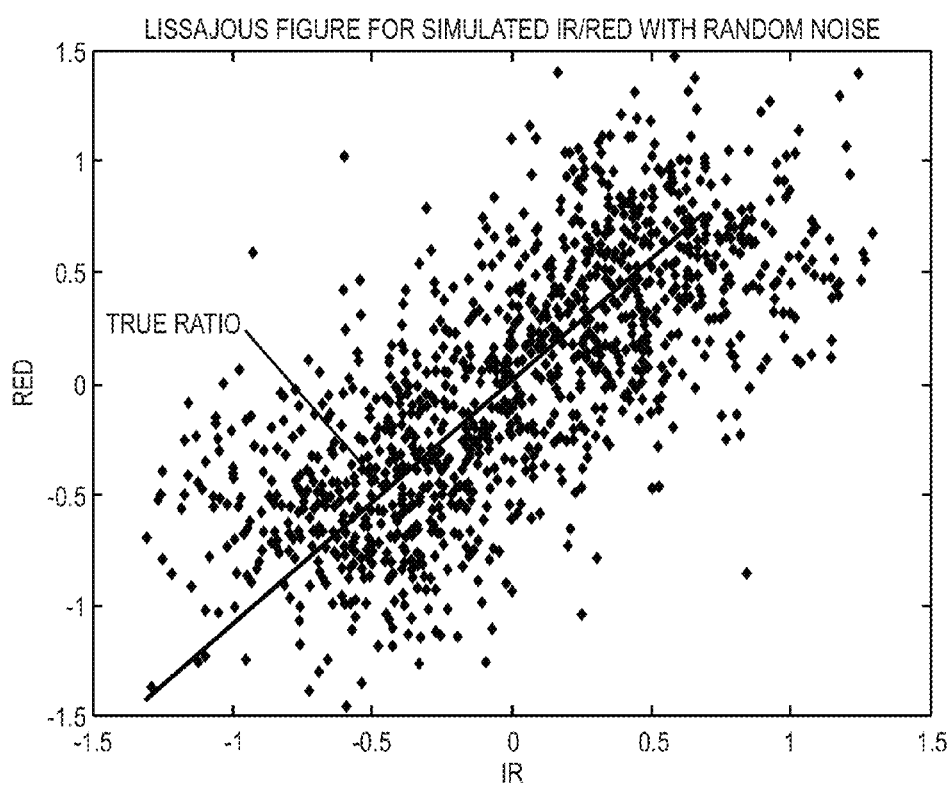
FIG. 6 is a Lissajous plot illustrating angle distribution for a simulated IR and red plethysmographic signal.
Figure 7A:
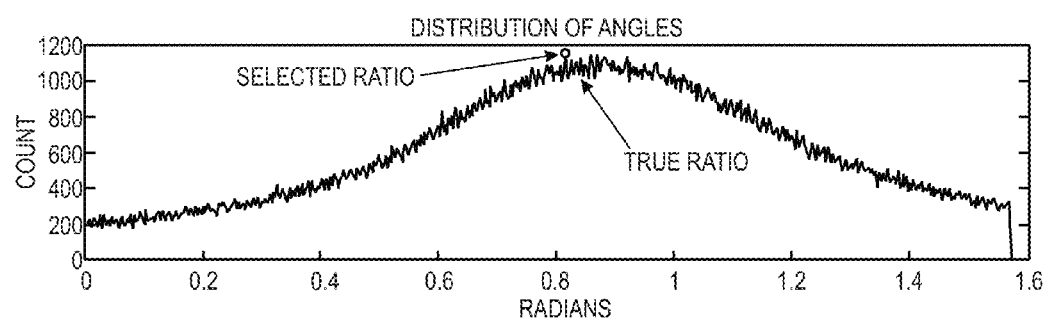
FIG. 7A illustrates a distribution of angles for the simulated signal of FIG. 6 in accordance with an embodiment of the present disclosure.
Figure 7B:
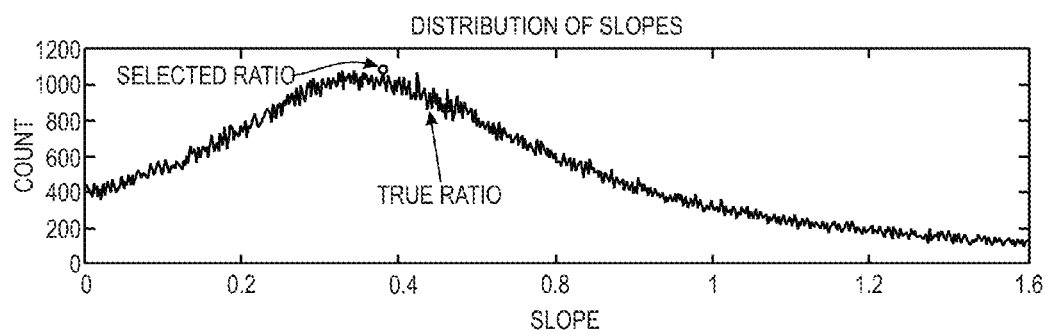
FIG. 7B illustrates a distribution of slopes for the simulated signal of FIG. 6 in accordance with an embodiment of the present disclosure.

In an example, simulated IR and red plethysmographic signals with a Red/IR ratio of 1.1 were generated in Matlab. Gaussian white noise was added to both channels at a signal to noise ratio of 1 to 1. Because simulated signals were used, a true ratio was known. A distribution of angles from all points to all other points, shown in FIG. 7A, was then generated from Lissajous figures of the red and IR signals (see FIG. 6). A second distribution was created from all point to point slopes and is shown in FIG. 7B. The slope distribution in FIG. 7B is skewed towards zero, which results in a larger error between the selected ratio (peak of distribution) and the true ratio. The ratio as calculated by angle distribution exhibits closer correlation to the true ratio relative to the slope distribution method and does not possess this skewed behavior.

The present techniques may be applied to any Lissajous method, or any method for determining an angle characteristic from a data scatter plot. In one embodiment, a Lissajous figure may represent different types of signals. For example, a Lissajous figure may represent a photoplethysmography signal taken at a first body site (e.g., an IR photoplethysmography signal measured at a patient's ear) and a photoplethysmography signal taken at a second, different body site (e.g., an IR photoplethysmography signal measured at a patient's finger). This angle characteristic may then be used to determine a true slope or an approximation to a true slope or some other slope. Further, the present techniques may also be applied to determine an angle characteristic to data scattered in two or more directions. In addition, in certain embodiments, the techniques may be used in conjunction with multiple Lissajous figures as, for example, generated by a wavelet transform method of determining respiration rate or $SPO_2$. In other embodiments, similar results may be achieved by non-linearly changing the width of the bins used in the distribution of gradients method. Such a nonlinear change of bin widths in any distribution may change the characteristic points in the distribution, and this may be used to remove an algorithmic biasing of the expected result.

Figure 8:
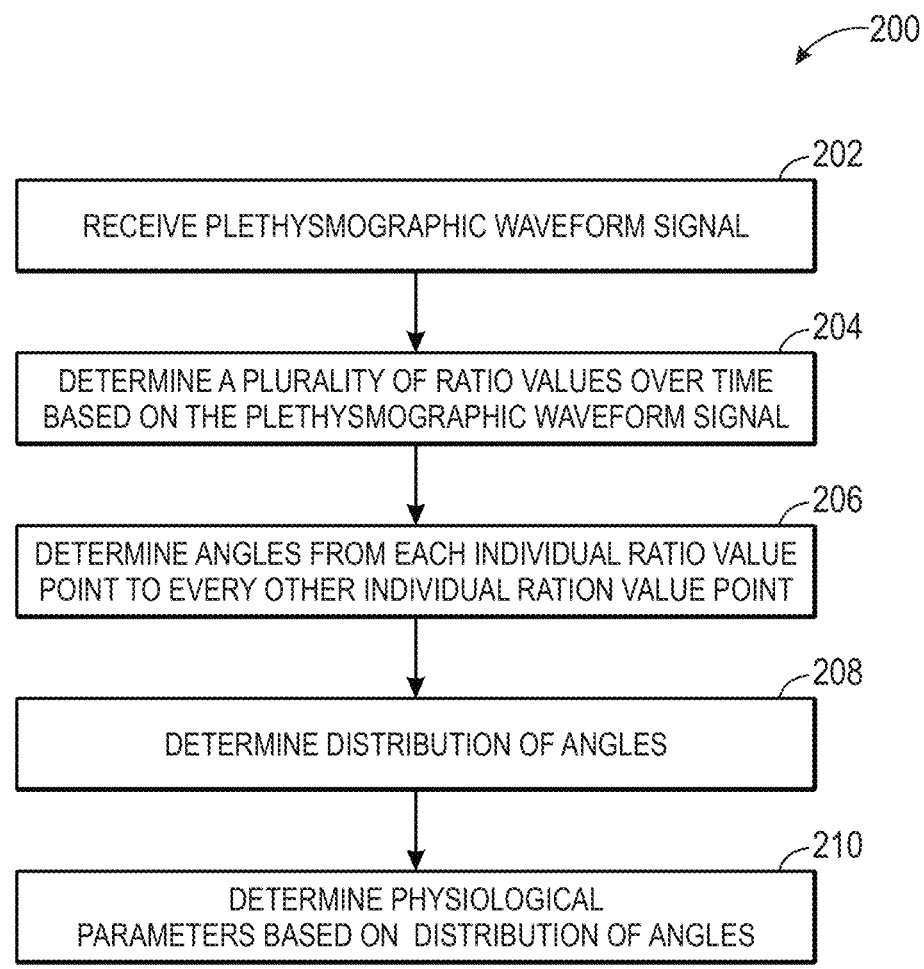
FIG. 8 is a method of assessing a plethysmographic signal in accordance with embodiments of the present disclosure.

FIG. 8 is a process flow diagram illustrating a method 200 in accordance with some embodiments. The method may be performed as an automated procedure by a system, such as system 10. In addition, certain steps of the method may be performed by a processor, or a processor-based device such as a patient monitor 14 that includes instructions for implementing certain steps of the method 200. According to an embodiment, the method 200 begins with obtaining a plethysmographic waveform signal from a pulse oximetry sensor 12 at step 202.

The monitor 14 may determine a plurality of ratio values over time based on the plethysmographic waveform signal at step 204. In one embodiment, the ratio values are a ratio of a red signal versus an IR signal. In other embodiments, the ratio may be a ratio of a primary signal and a reference signal. At step 206, the ratio values may be plotted and the angles between each individual point to every other point may be determined. For example, the angles may be determined based on a Lissajous plot of the ratio values. From the plotted points in the Lissajous, a number of angle values may be determined. At step 208, a distribution of the determined angles may be generated and at step 210, a physiological parameter may be determined based on the distribution of angles. For example, a peak of the distribution may be used as a ratio of ratios for determining a blood oxygen saturation, such as provided in the techniques disclosed in U.S. Pat. No. 8,007,441, which is incorporated by reference in its entirety herein for all purposes.

In one embodiment, the plethysmographic waveform may be processed by analyzing a wavelet transformed plethysmographic signal. Information derived from the transform of the plethysmographic signal (i.e., in wavelet space) may be used to provide measurements of one or more physiological parameters. Accordingly, the wavelet-transformed signal may be used to generate a Lissajous plot or other representation of ratio values as provided herein.

The continuous wavelet transform of a signal x(t) in accordance with the present disclosure may be defined as $$T(a, b) = \frac{1}{\sqrt{a}} \int_{-\infty}^{+\infty} x(t) \psi^* \left( \frac{t-b}{a} \right) dt \quad (1)$$

where $\psi^*(t)$ is the complex conjugate of the wavelet function $\psi(t)$, a is the dilation parameter of the wavelet and b is the location parameter of the wavelet. The transform given by equation (1) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transmit values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (2)$$

where '||' is the modulus operator. The scalogram may be resealed for useful purposes. One common resealing is defined as $$S_R(a, b) = \frac{|T(a, b)|^2}{a} \qquad (3)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane is labeled a "maxima ridge".

For implementations involving fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by √(a).

In the discussion of the techniques herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (4)$$

where $f_c$ the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Monet wavelet, is defined as:

$$\psi(t)=\pi^{-1/4}(e^{i2\pi f_0 t}-e^{-(2\pi f_0)^2/2})e^{-t^2/2} \qquad (5)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Monet wavelet can be written in a simpler form as $$\psi(t) = \frac{1}{\pi^{1/4}} e^{i2\pi f_0 t} e^{-t^2/2} \qquad (6)$$

This wavelet is a complex wave within a scaled Gaussian envelope. While both definitions of the Morlet wavelet are included herein, the function of equation (6) is not strictly a wavelet as it has a non-zero mean (i.e., the zero frequency term of its corresponding energy spectrum is non-zero). However, it will be recognized by those skilled in the art that equation (6) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of plethysmographic signals may be used to provide clinically useful information within a medical device.

Pertinent repeating features in a signal give rise to a time-scale band in wavelet space or a resealed wavelet space. For example, the pulse component of a plethysmographic signal produces a dominant band in wavelet space at or around the pulse frequency. FIGS. 9A and B show two views of an illustrative scalogram 250 derived from a plethysmographic signal, according to an embodiment. The figures show an example of the band 252 caused by the pulse component in such a signal. The pulse band is located between the dashed lines in the plot of FIG. 9A. The band is formed from a series of dominant coalescing features across the scalogram. This can be clearly seen as a raised band across the transform surface in FIG. 9B located within the region of scales indicated by the arrow in the plot (corresponding to 60 beats per minute). The maximum of this band with respect to scale is the ridge. The locus of the ridge is shown as a black curve on top of the band in FIG. 9B. By employing a suitable resealing of the scalogram, such as that given in equation (3), the ridges found in wavelet space may be related to the instantaneous frequency of the signal. In this way, the pulse rate may be obtained from the plethysmographic signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 9C:
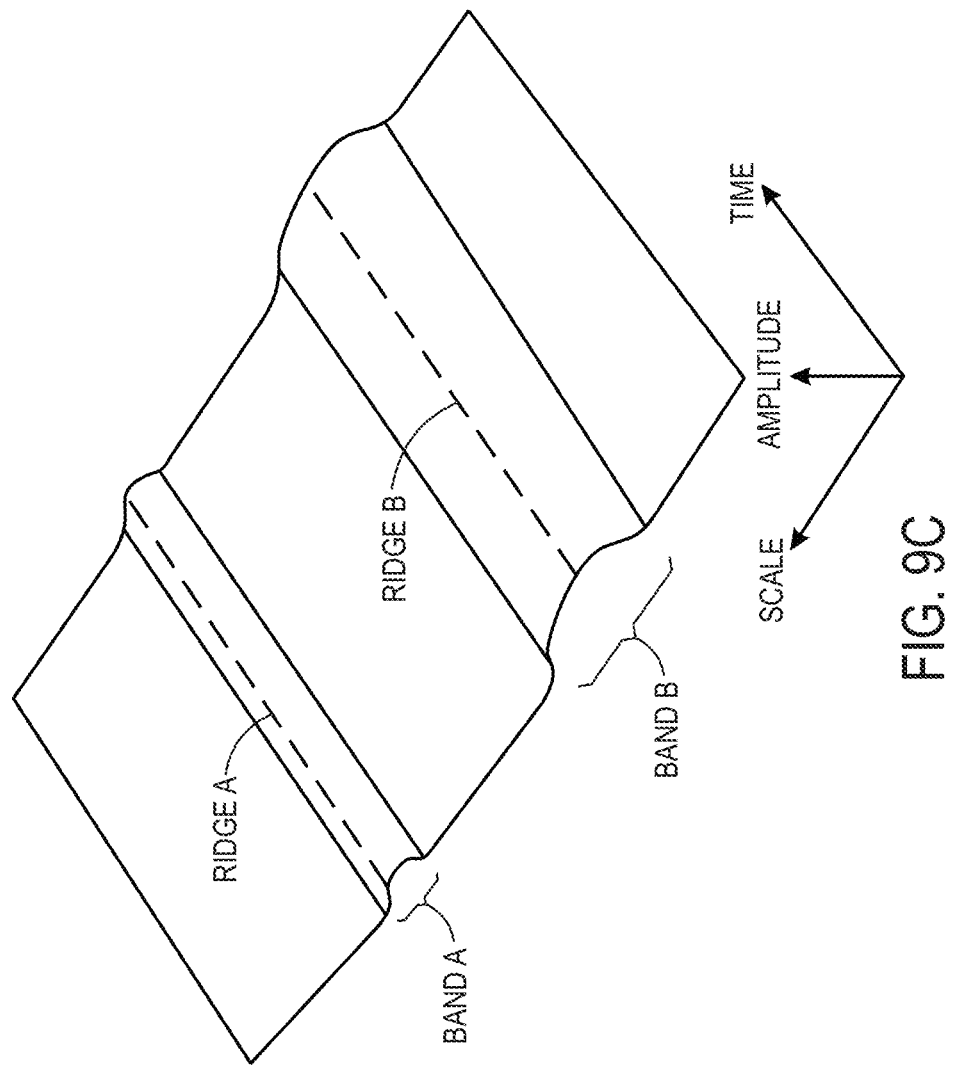
FIG. 9C shows an illustrative scalogram derived from a signal containing two pertinent components in accordance with an embodiment.
Figure 9D:
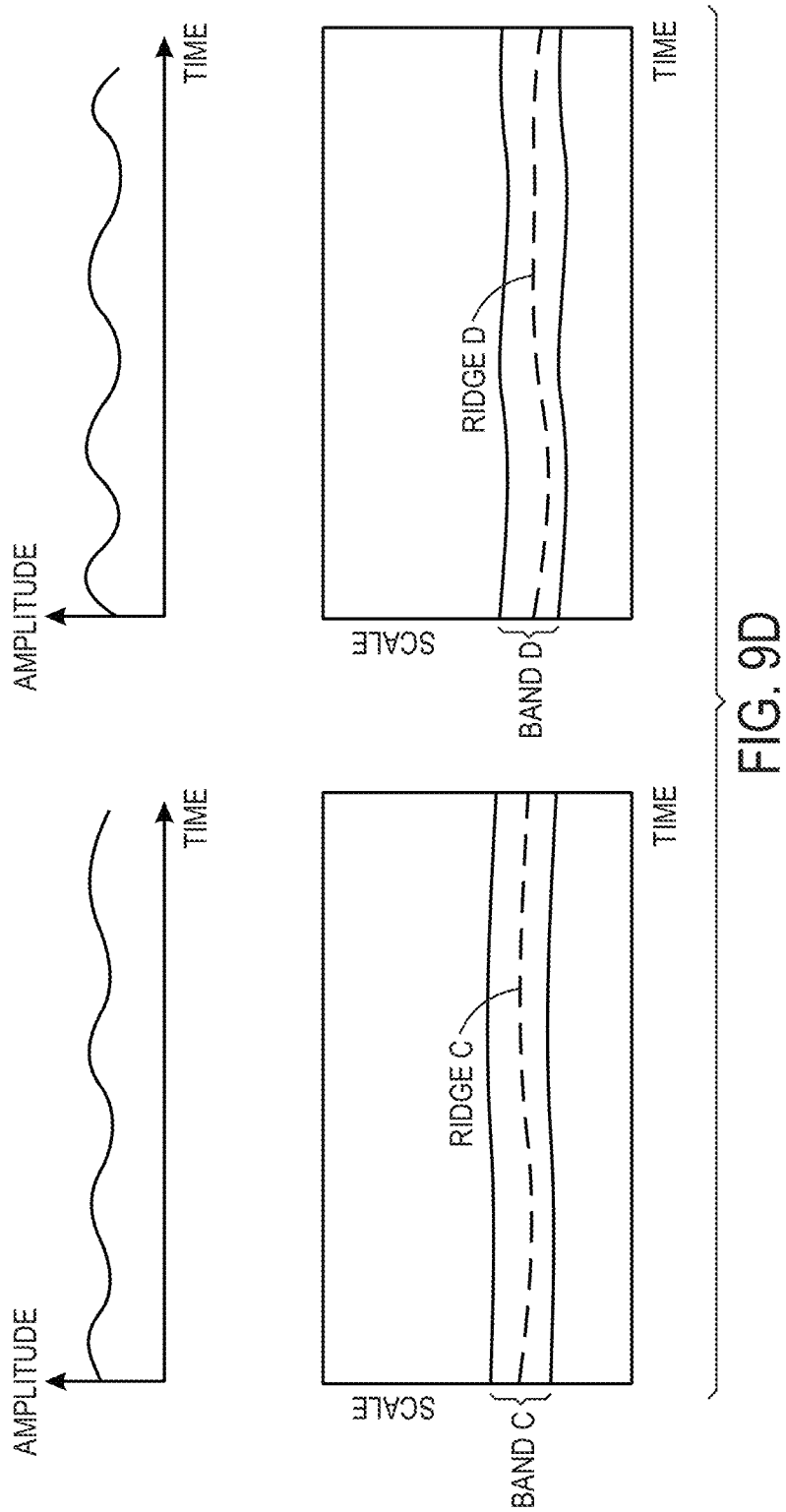
FIG. 9D shows an illustrative schematic of signals associated with a ridge in FIG. 9C and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 9C shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band." In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 9D show a schematic of the RAP and RSP signals associated with ridge A in FIG. 9C. Below these RAP and RSP signals are schematics of a further wavelet decomposition of these newly derived signals. This secondary wavelet decomposition allows for information in the region of band B in FIG. 9C to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 9C) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (7)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (8)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (9)$$

A continuous wavelet transform may be used to transform a plethysmographic signal and determine a physiological parameter, such as blood oxygen saturation, respiration rate, fluid responsiveness, or an arrhythmia indicator.

In one embodiment, the amplitude of the respiratory sinus arrhythmia (RSA) component of the plethysmographic signal may be analyzed to determine information related to fluid responsiveness. Changes in the amplitude of the RSA component correlate with changes in the level of fluid responsiveness. For example, the RSA component may be derived from the pulse band ridge, such as pulse band ridge 254 in FIG. 9B, of the scalogram. Further, any band in the transform space indicative of pulse period may provide information for measuring RSA, such as a band at a scale above that of the pulse band, which, though of lower amplitude, may clearly indicate RSA. The amplitude modulation of the RSA may correlate with the amplitude modulation of the pulse band ridge. By measuring the amplitude variation of the pulse band ridge, the local modulation of the RSA waveform may be extracted. The RSA occurs naturally in the variation in the periodicity of the heart beat timing over the respiration cycle. The amplitude modulation of other components of the scalogram indicative of pulse period may be used to measure RSA in place of or in addition to the amplitude modulation of the pulse band ridge.

The techniques provided herein have been illustrated with reference to the monitoring of a physiological signal (which may be a photoplethysmographic signal); however, it will be understood that the disclosure is not limited to monitoring physiological signals and is usefully applied within a number of signal monitoring settings. Those skilled in the art will recognize that the present disclosure has wide applicability to other signals including, but not limited to, other biosignals (e.g., electrocardiogram, electroencephalogram, electrogastrogram, electromyogram, heart rate signals, pathological sounds, ultrasound, or any other suitable biosignal), and/or any other suitable signal, and/or any combination thereof.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims. Further, it should be understood that elements of the disclosed embodiments may be combined or exchanged with one another.

What is claimed is:

1. A method for determining a physiological parameter, comprising:
using a processor:
receiving a signal from a sensor, wherein the signal comprises at least two components;
determining a plurality of angles formed by a respective plurality of individual points of a Lissajous plot derived from the at least two components and wherein the angles comprise angles formed between a first line passing through an initial point selected from the plurality of individual points of the Lissajous plot and a second line passing through an individual point selected from another of the plurality of individual points of the Lissajous plot and the initial point;
determining a distribution of the angles; and
determining a physiological parameter based at least in part on the distribution of the angles.

2. The method of claim 1, wherein the Lissajous plot is derived from a logarithm of the components of the signal.

3. The method of claim 1, wherein determining the physiological parameter based on the distribution of the angles comprises determining a peak or mean of the distribution or a combination thereof.

4. The method of claim 1, wherein the physiological parameter comprises a blood oxygen saturation.

5. The method of claim 1, wherein the physiological parameter comprises a measure of arrhythmia.

6. The method of claim 1, wherein determining a physiological parameter of a patient comprises determining a pulse rate, respiration rate, respiration effort, continuous non-invasive blood pressure, cardiac output, fluid responsiveness, perfusion, pulse rhythm type, hydration level, or any combination thereof.

7. The method of claim 1, wherein the at least two components comprise an infrared channel and a red channel.

8. The method of claim 1, comprising determining a signal quality metric by comparing a signal quality of the signal received from the sensor to a predetermined threshold.

9. The method of claim 8, comprising determining the distribution of the angles when the signal quality is below the predetermined threshold.

10. The method of claim 9, comprising determining the physiological parameter based at least in part on the distribution of the slopes when the signal quality is above the predetermined threshold.

11. A patient monitoring system, comprising:
a patient monitor comprising a processor configured to:
receive a plethysmographic signal from a sensor;
determine a plurality of ratio values related to the signal at a plurality of time points;
determine a distribution of gradients between the plurality of ratio values;
determine angles between each of the plurality of ratio values based at least in part on a position of the plurality of ratio values relative to one another;
determine a distribution of the angles;
compare a first mean and/or peak ratio value determined based on the distribution of the angles to a second mean and/or peak ratio value determined based on the distribution of gradients;
determine a physiological parameter based at least in part on the distribution of the angles; and
determine a confidence of a value of the physiological parameter based on the comparing of the first mean and/or peak value to the second mean and/or peak value.

12. The system of claim 11, wherein the processor is configured to determine a signal quality of the plethysmographic waveform signal based on a difference between the first mean and/or peak ratio value and the second mean and/or peak ratio value.

13. The system of claim 11, wherein the processor is configured to determine a second physiological parameter based at least in part on the distribution of gradients between the plurality of ratio values.

14. The system of claim 11, wherein the processor is configured to determine the physiological parameter based at least in part on the distribution of gradients between the plurality of ratio values if a signal quality metric is above a predetermined threshold and wherein the processor is configured to determine the physiological parameter based at least in part on the distribution of the angles if the signal quality metric is below the predetermined threshold.

15. The system of claim 11, wherein the patient monitor comprises a display configured to provide an indication related to the physiological parameter.

16. The method of claim 1, wherein the Lissajous plot is derived from a wavelet transform.

* * * * *